United States Patent
Köhler

(10) Patent No.: US 8,310,250 B2
(45) Date of Patent: Nov. 13, 2012

(54) PROBE AND ARRANGEMENT FOR DETERMINING THE MOISTURE CONTENT OR CONDUCTIVITY OF A MATERIAL

(75) Inventor: Kurt Köhler, Ettlingen (DE)

(73) Assignee: Imko intelligente Micromodule Köhler GmbH, Ettlingen (DE)

( * ) Notice: Subject to any disclaimer, the term of this patent is extended or adjusted under 35 U.S.C. 154(b) by 430 days.

(21) Appl. No.: 12/660,288

(22) Filed: Feb. 24, 2010

(65) Prior Publication Data
US 2010/0225338 A1    Sep. 9, 2010

(30) Foreign Application Priority Data
Mar. 5, 2009   (DE) .......................... 10 2009 011 278

(51) Int. Cl.
*G01R 27/08*    (2006.01)

(52) U.S. Cl. ........................................ 324/696; 324/694
(58) Field of Classification Search ................. 324/696, 324/694, 689
See application file for complete search history.

(56) References Cited

U.S. PATENT DOCUMENTS 7,292,155 B2 * 11/2007 Vokey et al. .................. 340/602
2004/0244482 A1 * 12/2004 Schultz ...................... 73/335.01

* cited by examiner

*Primary Examiner* — Vincent Q Nguyen
(74) *Attorney, Agent, or Firm* — Klaus J. Bach

(57) ABSTRACT

In a probe and an arrangement including a probe for determining a moisture content or a conductivity of a material, wherein the probe has a base body with two electrical conductors of which at least one has the form of a tape which is embedded in an electrically insulating material area of the base body in such a way that only an edge area of the tape-like conductor is disposed at the surface of the insulating material area of the base body for contact with the material.

11 Claims, 4 Drawing Sheets

PROBE AND ARRANGEMENT FOR DETERMINING THE MOISTURE CONTENT OR CONDUCTIVITY OF A MATERIAL

BACKGROUND OF THE INVENTION

The present invention relates to a probe for determining the moisture content or the conductivity of a material including a body which has at least two electrical conductors which extend in parallel relationship and of which at least one is in the form of a tape. The invention also resides in an arrangement for determining the moisture content of a material.

Such a probe or, respectively, such an arrangement has been offered and successfully marketed by Applicant for many years. In addition, such a probe is known for example from DE 43 34 649 A1.

The probes offered by Applicant for example under the designation GS1 and GS2 have a parallelepiped metallic body which, at one side thereof, has a longitudinally extending recess of rectangular cross-section. The recess is covered by a plate consisting of a plastic material which is provided, at its side facing away from the recess, with an electric conductor consisting of a steel tape. The metallic base body which also serves as an electric conductor forms with an electrically conductive steel tape a measuring line, which is needed for determining the moisture content of a material via the so-called Time-Domain-Reflectometry (TDR) principle.

A method and an arrangement which operates in accordance with the TDR principle is known for example from EP 0 478815 A1. In the known process, a rectangular signal is applied to the measuring line by means of a measuring signal transmitter. The pulse duration of the signal is greater than twice the travel time of the signal in the measuring line. The signal is reflected on, or at the end of the measuring line. At the input end of the measuring line or, respectively, the output of the measuring signal transmitter, a summing signal is formed by superposition of the respective amplitudes of the signal fed into the measuring line and the signal reflected at the end of the measuring line.

Although generally the known methods or, respectively, the known devices deliver very good results, they still have the disadvantage—also the probes marketed by Applicant—that, in connection with materials of high conductivity, they do not provide satisfying results in every case. In particular, the moisture in fresh concrete cannot be determined with the known probes in a satisfying manner.

It is the object of the present invention to provide a probe like the one described above or the arrangement referred to above in such a way that it becomes suitable as a measuring probe for determining the moisture content of a material which has a high conductivity.

SUMMARY OF THE INVENTION

In a probe or an arrangement for determining a moisture content or a conductivity of a material, which probe or arrangement comprises a base body including two electrical conductors of which at least one has the form of a tape, the base body includes an electrically insulated area in which at least the tape-like conductors is disposed.

Since the base body includes an electrically insulating area in which at least the tape-like conductor is arranged, the conductor comes no longer into intense contact with the material. This, on one hand, has the advantage that the conductor is protected from wear as it may occur for example by abrasive contacts so that, as a result, the geometric dimensions of the conductor remain essentially unchanged which is advantageous with respect to the measuring accuracy. On the other hand, since the conductor does not come into contact with the material the galvanic contact with the material to be measured is substantially reduced without detrimental effects since the impedance needed for the arrangement is low anyhow.

It is advantageous if the tape-like conductor extends in its transverse direction into the electrically insulating area. That is, the conductor extends from a planar surface of the probe or, respectively, the electrically insulating area preferably normally into the interior of the electrically insulating area. In this way, the tape-like conductor comes in contact with the material, if at all, only along its narrow side. As a result, wear affects only the narrow width of the tape-like conductor which has little effect on the measuring accuracy. Even during use in highly abrasive materials, the resulting wear has such little effect that subsequent adjustments or respectively recalibrations are only rarely necessary. Because of the fact that the tape-like conductor comes in contact with the material only along the side thereof, also the galvanic contact with the medium or material to be measured is minimized in a simple way. As a result, advantageously materials with high conductivity as for example fresh concrete may be examined.

In a further particular embodiment of the invention, the tape-like conductor is arranged between two elements which consist of an electrically insulating material. This substantially simplifies the manufacture of the probe, since such an arrangement is easy to assemble. After the conductor is arranged between the elements, the elements, respectively, the arrangement can be cemented together.

An embodiment of the invention wherein the base body has an electrically conductive frame, in which the electrically insulating structure is arranged, has been found to be particularly advantageous. The frame forms an electrical conductor which, together with the tape-like conductor, serves as measuring line which requires a device operating in accordance with the TDR principle. It is particularly advantageous for obtaining good measuring results if the frame fully surrounds the tape-like measuring conductor.

Advantageously, the frame consists of tool steel with a Rockwell hardness of at least HRC-40 and particularly at least HRC-50. Then the frame is very resistant to wear so that the probe can also be used for measuring a hard material such as fresh concrete.

In a further embodiment of the invention, the electrically insulating elements consist of ceramics. Also, in this way, it is prevented that the shape of the probe is substantially changed by wear.

An embodiment of the invention wherein the tape-like conductor is comb-shaped has been found to be particularly advantageous. With the comb-like shape of the conductor, the area over which the conductor comes into galvanic contact with the material is substantially reduced. This is advantageous for the determination of the moisture content of a material with high conductivity such as for example fresh concrete. The teeth of the comb extend with respect to the longitudinal direction of the tape-like conductor at an angle of less than 90°. This, too, is advantageous for the measuring result. It is particularly advantageous if the angle is so selected that the teeth do not overlap as seen in the transverse direction of the tape.

In a further special embodiment of the invention, the base body is in the form of a flat parallelepiped and has at its side remote from the electrically insulated area, a window in which a cover element is arranged which consists of an insulating material. Since the base body is very flat, it can easily be inserted into a material. The parallelepiped base body may have at one front end a narrowing area whereby a wedge-like lance is formed which facilitates the insertion into a material. With the base body being provided at its side opposite the electrically insulated area, with a window in which a cover element of an electrically insulating material is arranged, it can be very flat without this detrimentally affecting the measuring results.

In a further special embodiment of the invention, the base body is in the form of a cylinder which is flattened at one side thereof and the electrically insulating is arranged at the flattened side. Since, in this case, the base body has essentially a cylindrical shape, it can be inserted into a cylindrical tube whose end extends for example into a moving medium or material. With the cylindrical shape, the sensor is rotatable within the tube. In this way, the angular position of the flattened side with respect to the direction of movement of the medium is adjustable. The probe position can therefore be optimized for measurements in a simple manner.

The invention will become more readily apparent from the following description of particulars and advantageous features thereof on the basis of the accompanying drawings.

DESCRIPTION OF VARIOUS EMBODIMENTS

Figure 1:
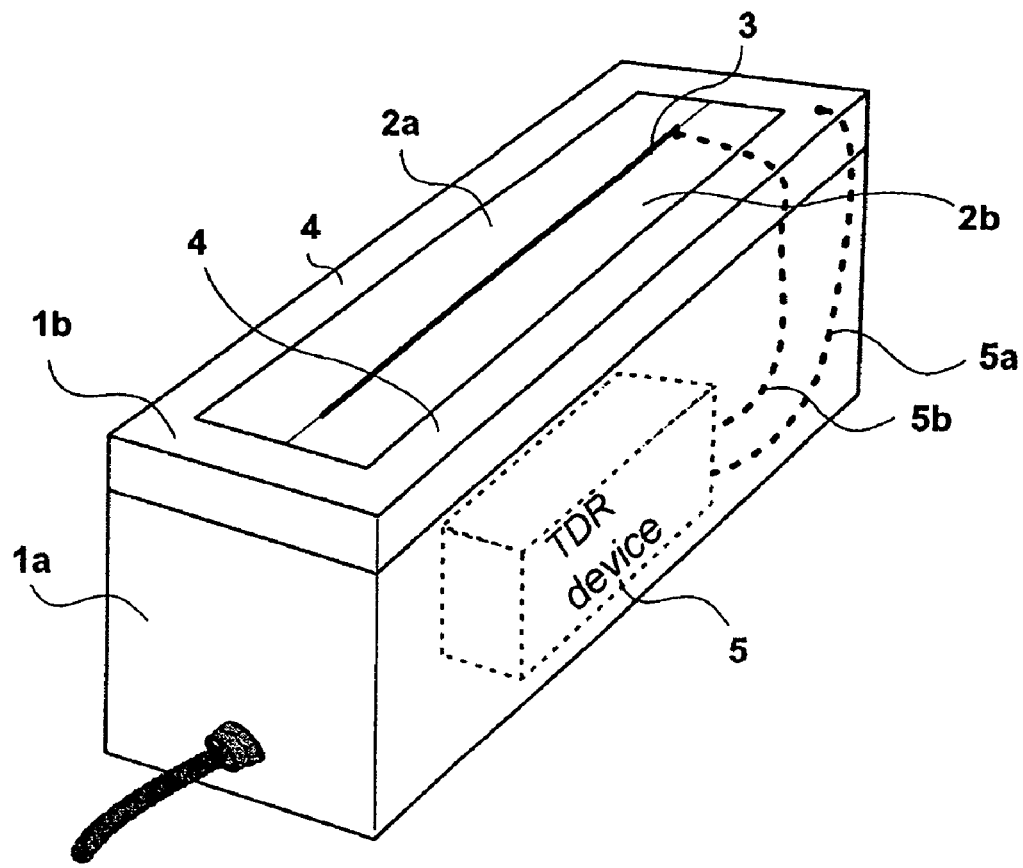
FIG. 1 shows schematically a first embodiment of the probe according to the invention.

As apparent in particular from FIG. 1, a probe comprises a base body 1a, 1b, which consists of a parallelepiped base part 1a and a frame 1b disposed thereon. The base part 1a consists of steel, for example V2A. At its side facing the frame 1b, the base body 1a has an about 15 mm deep cavity whose length and width are slightly smaller than the corresponding dimensions of the frame 1b. The frame 1b consists of tool steel with a Rockwell hardness of about HRC-60.

Within the frame, two elongated rectangular elements 2a, 2b of a ceramic material are arranged between which an electric conductor 3 in the form of a steel tape is disposed. The width of the conductor 3 is slightly greater than the thickness of the frame 1b. The thickness of the elongated ceramic elements 2a, 2b corresponds to the thickness of the frame 1b so that the side edge of the tape-like electrical conductor 3 projects slightly from the ceramic elements 2a, 2b into the body 1a. In this way, the electrical conductor 3 can easily be connected to a connecting line.

The longitudinal sides 4 of the frame 1b form with the electrical conductor 3 a measuring line as it is required for a device operating in accordance with the TDR principle for determining the moisture content or the conductivity of a material.

As indicated in FIG. 1, at least part of a device 5 for determining the moisture or conductivity of a material may be arranged in the base part 1a. The device 5 is connected to the frame 1b via a first connecting line 5a and to the tape-like electrical conductor 3 via a second connecting line 5b.

Figure 2:
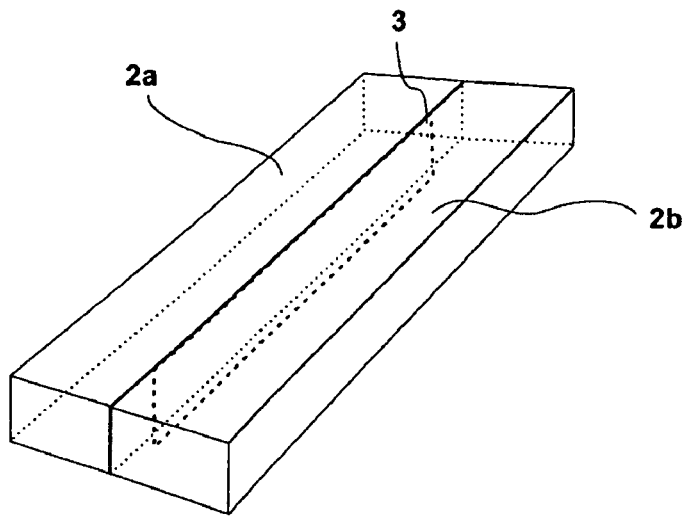
FIG. 2 shows the electrically insulating area of the probe shown in FIG. 1 with a tape-like conductor disposed therein.

As shown particularly in FIG. 2, the tape-like electrical conductor 3 projects at the side adjacent (facing) the base body 1a from the ceramic elements 2a, 2b. The arrangement consisting of the ceramic elements 2a, 2b and the tape-like electrical conductor 3 are cemented together so that any gap between the two ceramic elements 2a, 2b is closed.

Figure 3A:
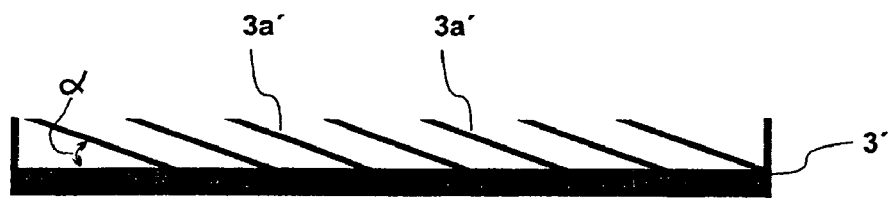
FIG. 3a shows a particular embodiment of a tape-like electrical conductor.
Figure 3B:
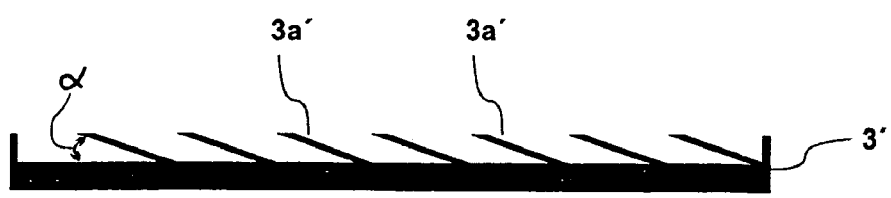
FIG. 3b shows the tape-like conductor of FIG. 3a after having been subjected to abrasive wear.

As shown particularly in FIGS. 3a and 3b, the tape-like electrical conductor 3' may be comb-shaped. The teeth 3a' of the comb-shaped tape-like conductor 3' project from a web extending in the longitudinal direction of the tape-like electrical conductor 3' at an angle α of about 20°. In this way, the teeth 3a' of the electrical conductor 3' do not essentially overlap as viewed in the transverse direction of the electrical conductor 3'.

In the electrical comb-shaped conductor 3' as shown in FIG. 3a, which was not yet exposed to abrasive wear, the teeth 3a' overlap slightly. In the conductor 3' shown in FIG. 3b, which was already subjected to abrasive wear, there is an area where the teeth 3a' do no longer overlap in transverse direction (projection).

Since with the comb-shaped electrical conductor 3' only the front ends of the teeth 3a' come into contact with the material to be measured good results are obtained in materials of very high conductivity. By the relatively small galvanic contacts of the electrical conductor 3' with the material, only a small signal attenuation is obtained which is advantageous. The inclined arrangement of the teeth is very advantageous. It has been found, surprisingly, that, with the comb-shaped electrical conductor 3', the necessary and relatively low impedance of the measuring conductor arrangement is not, or essentially not, affected.

Figures 4A, 4B:
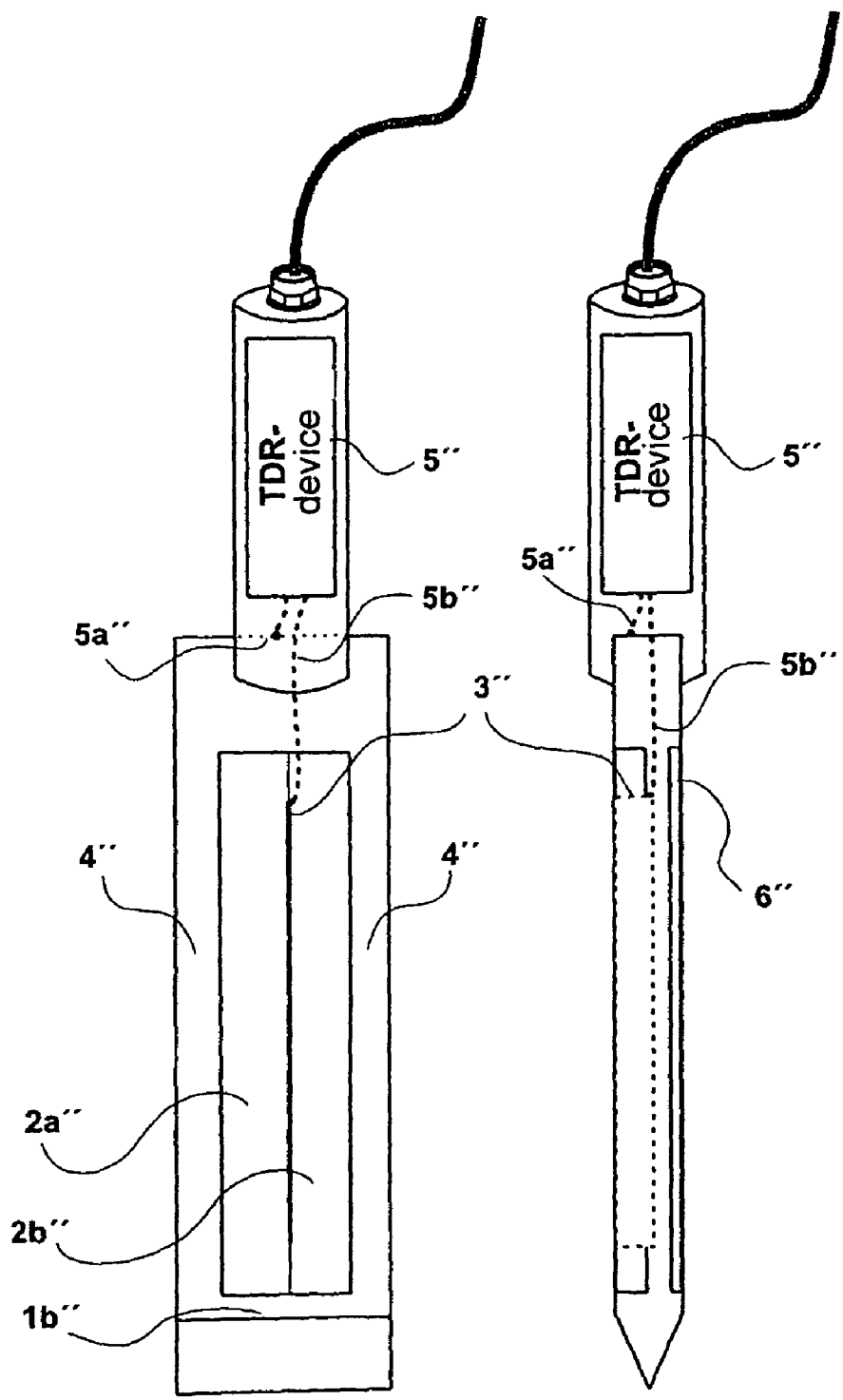
FIG. 4a shows schematically a second embodiment of a probe according to the invention as seen from the front, that is, the sensor side thereof.
FIG. 4b shows the probe of FIG. 4a in a side view.

In the embodiment of the probe according to the invention as shown in FIGS. 4a and 4b, the base body 1b" is a flat parallelepiped, which is wedge-shaped at one of its ends. The parallelepiped body further includes a rectangular window. In the window, the ceramic elements 2a", 2b" are arranged with the tape-like electrical conductor 3" disposed therebetween. At the side of the base body 1b" opposite the ceramic elements 2a", 2b" a cover element 6" is arranged which also consists of ceramic material.

The longitudinal sides 4" of the rectangular window form, together with the electrical conductor 3", a measuring line as it is required for a device for measuring the moisture or conductivity of a material operating according to the TDR principle.

At its end opposite the wedge-like end of the base body 16" a device 5 for determining the moisture content or the conductivity of the material is arranged. The device 5" is connected to the base body 1b" via a first connecting line 5a" and to the electrical conductor 3" via a second connecting line 5b".

Figure 5:
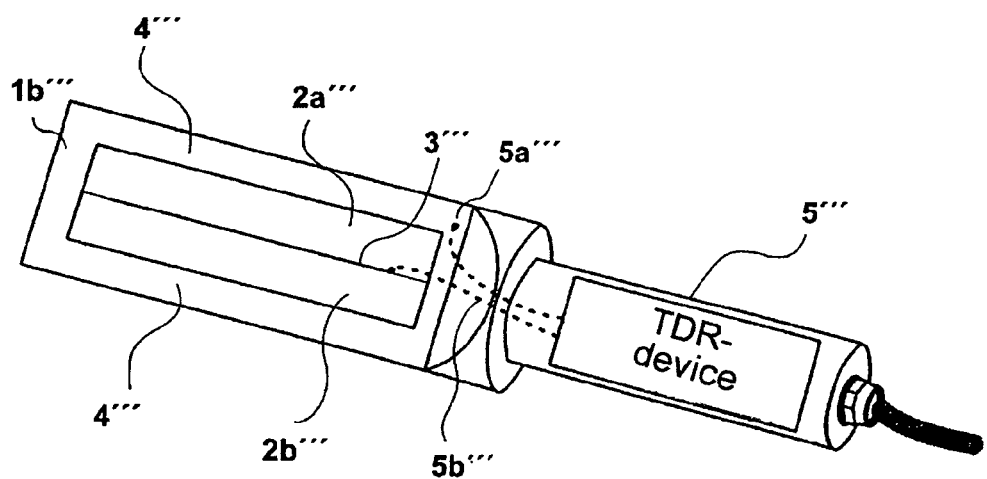
FIG. 5 shows schematically another embodiment of a probe according to the invention.

In the embodiment of the probe according to the invention as shown in FIG. 5, the probe is in the form of a cylinder, which is flattened at one side thereof. At its flattened side, the base body 1b''' has a rectangular cavity in which the ceramic elements 2a''', 2b''' are arranged with the tape-like electrical conductor 3''' disposed therebetween. The base body 1b''' consists of steel so that the walls 4''' of the rectangular recess which extend parallel to the electrical conductor 3''' form with the electrical conductor 3''' the measuring line.

At the front end of the base body 1b''', a device 5b''' for determining the moisture or the conductivity of a material is arranged, which device 5b''' is connected to the base body 1b''' via a first connecting line 5a''' and via a second connecting line 5b''' to the electrical conductor 3'''. With the cylindrical shape of the base body 1b''', the probe may be inserted into a flowing medium via a cylindrical tube. Since the probe is also cylindrical, it can be rotated within the tube so that the flattened side of the probe can be adjusted with respect to the flow direction of the medium.

What is claimed is:

1. A probe for determining a moisture content or conductivity of a material comprising:
   a base body (1a, 1b, 1b', 1b'', 1b''') including at least two electrical conductors (3, 4, 3', 3'', 4'', 3''', 4''') of which at least one (3, 3', 3'', 3''') is tape-like formed,
   said base body (1a, 1b, 1b'', 1b''') including an electrically insulating area (2a, 2b; 2a'', 2b'', 2a''', 2b''') in which the at least one tape-like electrical conductor is disposed so that, in its transverse direction, it extends from the surface of the base body (1a, 1b, 1b'', 1b''') into the electrically insulating area (2b; 2a'', 2b'', 2a''', 2b'''), whereby only a side edge surface of the tape like electrical conductor is exposed at the surface of the base body for contact with the medium.

2. The probe according to claim 1, wherein the at least one tape-like conductor (3, 3', 3'', 3''') is disposed between two elements (2a, 2b; 2a'', 2a''', 2b''') consisting of an electrically insulating material.

3. The probe according to claim 2, wherein the electrically insulating elements (2a, 2b, 2a'', 2b'', 2a''', 2b''') consist of a ceramic material.

4. The probe according to claim 1, wherein the base body (1a, 1b) includes an electrically conductive frame (1b) in which the electrically insulating area (2a, 2b) is arranged.

5. The probe according to claim 4, wherein the frame (1b) consists of tool steel having a Rockwell hardness of at least HRC-50.

6. The probe according to claim 1, wherein the at least one tape-like conductor (3') is configured so as to be comb-shaped including parallel teeth extending to the surface of the base body for contact with the medium.

7. The probe according to claim 6, wherein the comb-shaped conductor (3') has teeth (3a') which extend from the tape-like conductor at an angle ($\alpha$) of less than 90° with respect to the longitudinal direction of the conductor (3').

8. The probe according to claim 7, wherein the angle ($\alpha$) is so selected that—seen in a transverse direction of the conductor (3')—the teeth (3a') do not overlap.

9. The probe according to claim 1, wherein the base body (1b'') is parallelepiped in its shape and is provided at its side opposite the electrically insulating area (2a'', 2b'') with a window in which a cover element (6'') consisting of an electrically insulating material arranged.

10. The probe according to claim 1, wherein the base body (1b''') consists of a cylinder with a flattened side on which the electrically insulating area (2a''', 2b''') is arranged.

11. An arrangement for determining moisture or conductivity of a medium, including a probe comprising:
    a base body (1a, 1b, 1b', 1b'', 1b''') and, associated with the base body, at least two electrical conductors (3, 4, 3', 3'', 4'', 3''', 4''') of which at least one (3, 3', 3'', 3''') is tape-like formed, the base body having an electrically insulated material area (2a, 2b; 2a'', 2b'', 2a''', 2b''') in which the at least one tape-like electrical conductor is disposed; so that, in its transverse direction it extends from the surface of the base body (1a, 1b, 1b'', 1b''') into the interior thereof and is embedded in the electrically insulated material area to the extent that only a side edge surface of the tape-like electrical conductor (3, 3', 3'', 3''') is exposed at the surface of the base body for contact with the medium.

* * * * *